United States Patent

Kunz

[11] Patent Number: 5,504,433
[45] Date of Patent: Apr. 2, 1996

[54] ELECTROCHEMICAL SENSOR FOR MONITORING ELECTROLYTE CONTENT

[75] Inventor: Harold R. Kunz, Vernon, Conn.

[73] Assignee: International Fuel Cells Corporation, South Windsor, Conn.

[21] Appl. No.: 965,312

[22] Filed: Oct. 23, 1992

[51] Int. Cl.⁶ .................................................. G01N 27/12
[52] U.S. Cl. ........................................ 324/693; 324/446
[58] Field of Search ................................. 324/432, 439, 324/446, 450, 71.1, 693–715, 724; 73/53.05; 340/604, 605; 174/11 R

[56] References Cited

U.S. PATENT DOCUMENTS

| | | | |
|---|---|---|---|
| 3,721,970 | 3/1973 | Niemoth | 340/605 |
| 4,288,654 | 9/1981 | Blom et al. | 340/605 |
| 4,331,923 | 5/1982 | Akers, Jr. | 324/446 |
| 4,594,638 | 6/1986 | Suzuki et al. | 174/11 R |
| 4,682,156 | 7/1987 | Wainwright | 340/605 |
| 4,689,571 | 8/1987 | Yonezu et al. | 324/432 |
| 4,843,305 | 6/1989 | Akiba | 340/605 |
| 4,877,923 | 10/1989 | Sahakian | 174/11 R |
| 4,972,179 | 11/1990 | Akiba | 174/11 R |
| 5,109,202 | 4/1992 | Akiba | 340/605 |

FOREIGN PATENT DOCUMENTS

| | | | |
|---|---|---|---|
| 2025594 | 7/1979 | Germany | 324/446 |
| 2805161 | 8/1979 | Germany | 324/446 |
| 3006877 | 9/1981 | Germany | 324/446 |
| 0031836 | 10/1979 | Japan | 324/446 |
| 011148 | 6/1983 | Japan | 324/432 |
| 2311750 | 12/1990 | Japan | 324/446 |
| 311560 | 1/1991 | Japan | H01M 8/04 |

Primary Examiner—Maura K. Regan

[57] ABSTRACT

During operation of a fuel cell stack, electrolyte within individual fuel cells migrates between the cathode side and the anode side, and across the separator plate between the cathode side and the anode side electrolyte reservoir plate of a second cell. An electrochemical sensor comprised of wires, a sheath, and a porous conduit having a pore size distribution which is similar to that of the electrolyte reservoir plate in which the electrochemical sensor is located, is capable of determining the electrolyte content during fuel cell operation by measuring the electrical resistance between the wires. The conduit wicks electrolyte into its pores to a content similar to that of the electrolyte reservoir plate. This electrolyte establishes electrical contact between the wires such that the measure of the electrical resistance between the wires is related to the electrolyte content of the electrolyte reservoir plate.

24 Claims, 2 Drawing Sheets

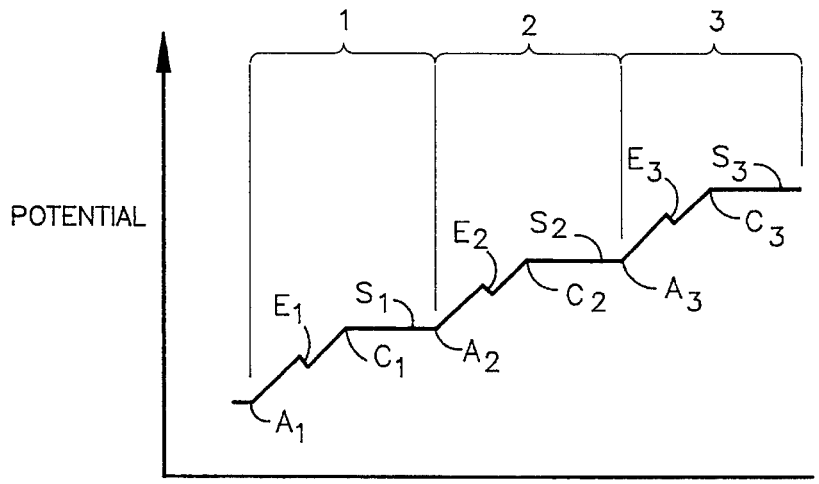
fig.1
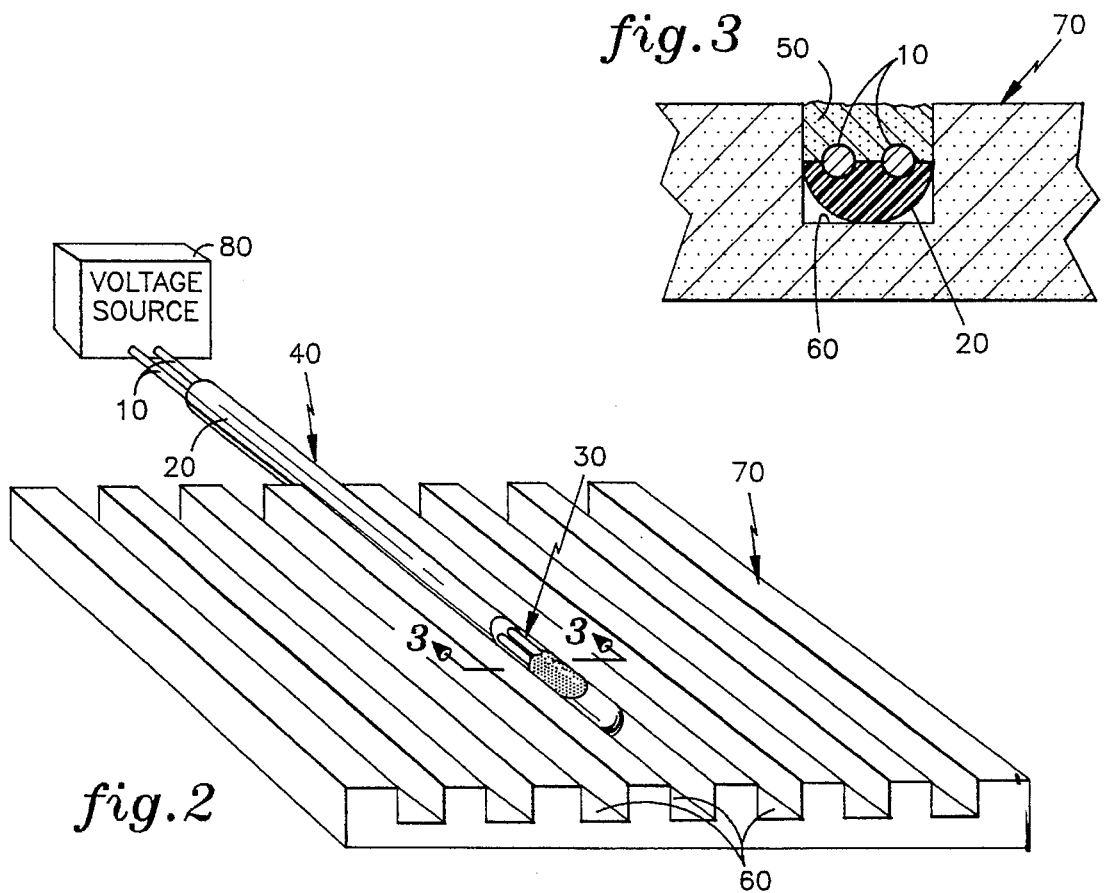
fig.2
fig.3

ELECTROCHEMICAL SENSOR FOR MONITORING ELECTROLYTE CONTENT

CROSS REFERENCE TO RELATED APPLICATION

Reference is hereby made to commonly owned U.S. Pat. No. 5,262,034 which discloses subject matter related to the subject matter of the present application.

TECHNICAL FIELD

The present invention relates to an electrochemical sensor, and especially to an electrochemical sensor for monitoring electrolyte content in an electrochemical cell.

BACKGROUND OF THE INVENTION

Many fuel cells used in the production of electricity contain, sequentially, an electrolyte reservoir plate, an anode chamber, an anode electrode, an electrolyte, a cathode electrode, a cathode chamber, a second electrolyte reservoir plate, and a separator plate. Several of these fuel cells are aligned in electrical series to form a fuel cell stack capable of producing electricity.

During operation of this fuel cell stack, electrolyte migrates both intra-cell and inter-cell due to the migration of ionic species in the electrolyte, thereby decreasing the volume of electrolyte (hereinafter referred to as electrolyte content) in one area of the fuel cell while increasing it in another. In a fuel cell that uses phosphoric acid as the electrolyte, positively charged protons are produced and consumed in each of the cells and the migration of the phosphate ion is effectively equivalent to the migration of the phosphoric acid electrolyte. Not only does the electrolyte migrate from the cathode side electrolyte reservoir plate within one cell of a stack to the anode of that cell, it may also migrate across the separator plate to another cell of the stack. This intra-cell migration can cause electrolyte flooding of the anode, thereby reducing the anode performance and the cell efficiency, while inter-cell migration can cause electrolyte flooding of end fuel cells in a fuel cell stack, thereby reducing performance of the stack and stack efficiency.

As the fuel cell operates, electrical potentials are created across individual phosphoric acid fuel cells and across the stack itself. These potentials are illustrated in FIG. 1 where the electrical potential increases from the anode of cell 1 ($A_1$) to the electrolyte at the anode of cell 1, decreases through the electrolyte of cell 1 ($E_1$) between the anode and cathode, and then again increases to the cathode of cell 1 ($C_1$). The potential then remains virtually constant from cell 1 to cell 2 across the cell 1 separator plate ($S_1$). Then, again, cell 2's potential increases from the anode ($A_2$) to the cathode ($C_2$). This sequence continues through the fuel cell stack to the end cell. Even though, as can be seen at $E_1$, $E_2$, and $E_3$, there is a slight decrease in potential across the electrolyte of each cell, the overall electrical potential of an individual cell increases from the anode to the cathode.

Due to the structure and complexity of a fuel cell stack, both the amount of electrolyte migration from the cathode side electrolyte reservoir plate to the anode side electrolyte reservoir plate of a single cell and the amount of inter-cell migration has been difficult to determine. If the migration over time is monitored in an operating fuel cell, a better understanding of this migration will develop, thereby shedding light upon possible solutions to the migration problem. Consequently, what is needed in the art is a means for monitoring electrolyte content such that the amount of migration of the electrolyte through individual cells and across cells in the fuel cell stack can be determined during fuel cell operation.

DISCLOSURE OF THE INVENTION

The present invention relates to an electrochemical sensor for measuring electrolyte content and to a method for monitoring electrolyte content in an electrolyte containing body. The electrochemical sensor comprises: at least two electrically conductive wires with sufficient space between these wires so as to prevent short circuiting of the wires, a porous, electrically non-conductive conduit in physical contact with the wires and having a similar pore size distribution as the electrolyte containing body, and a means for measuring electrical resistance between the wires.

The method for monitoring the electrolyte content in the electrolyte containing body comprises using the electrochemical sensor such that the conduit contacts an electrolyte containing body, wicking electrolyte into the conduit from the electrolyte containing body, applying a voltage across the wires, and measuring the electrical resistance between the wires. The electrical resistance between the wires is related to the content of electrolyte within the electrolyte containing body.

The foregoing and other features and advantages of the present invention will become more apparent from the following description and accompanying drawings.

BRIEF DESCRIPTION OF THE DRAWINGS

FIG. 1 is a graph representing the electrical potential profile across a fuel cell stack and the individual fuel cells located therein.

FIG. 2 is a schematic of one embodiment of the electrochemical sensor of the present invention located in a groove of a fuel cell electrolyte reservoir plate.

FIG. 3 is a cross-sectional view of the electrochemical sensor of FIG. 2.

Figure 4:
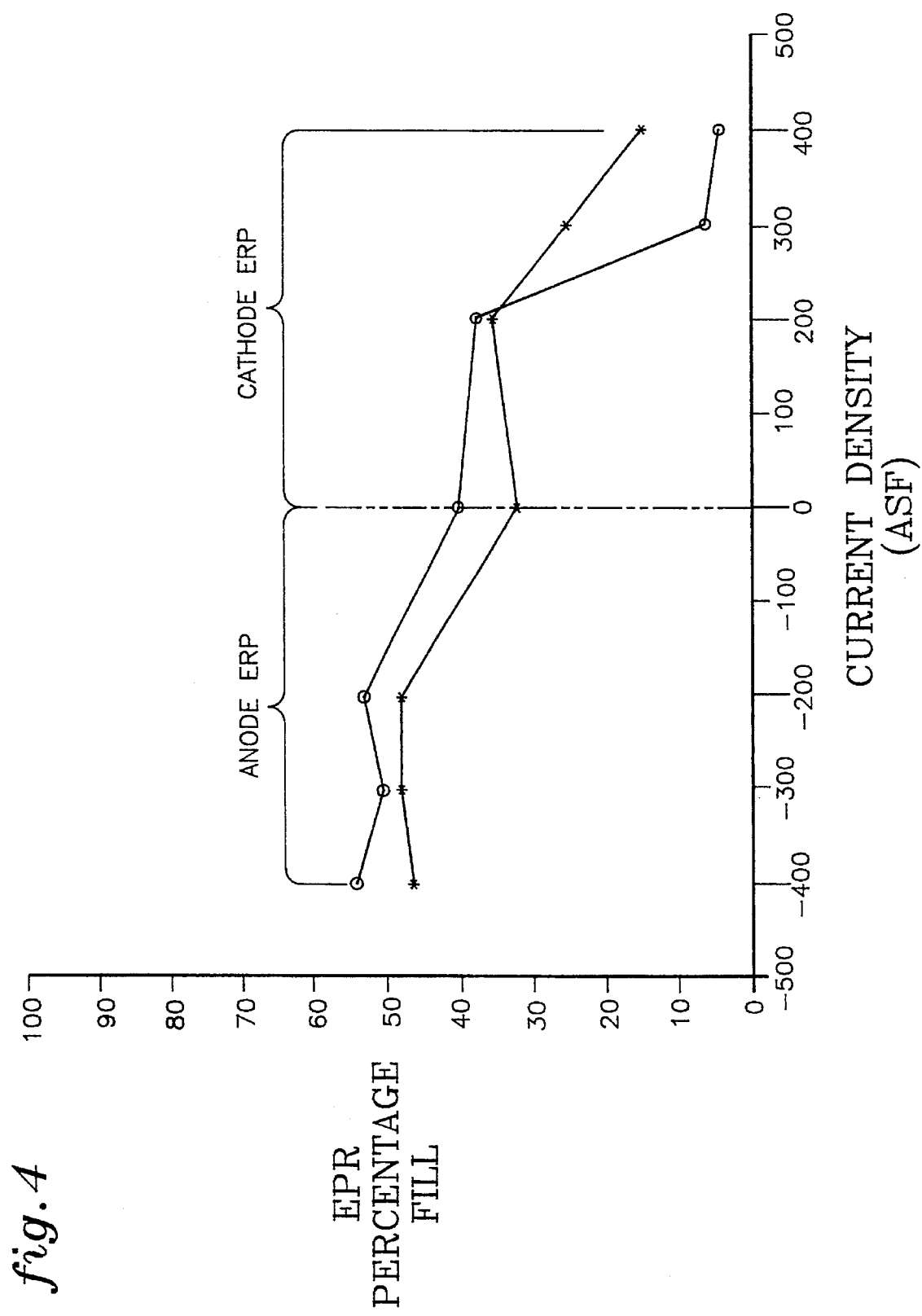
FIG. 4 is a graph of the effect of current density on electrolyte distribution in a fuel cell.

These figures are meant to be exemplary and not to limit the generally broad scope of the present invention.

BEST MODE FOR CARRYING OUT THE INVENTION

Referring to FIGS. 2 and 3, the electrochemical sensor 40 of the present invention comprises a pair of electrically conductive wires 10 substantially encapsulated within an electrically non-conductive sheath 20 with a porous, electrically non-conductive conduit 50 located in an opening 30 in the sheath 20 to provide a vehicle for electrolyte flow from the electrolyte reservoir plate 70 to the wires 10. As the content of electrolyte in the electrolyte containing body 70 increases or decreases, the electrolyte content in the conduit 50 similarly changes. This change in electrolyte content can be monitored and the electrolyte content can be determined by applying a voltage across to the wires 10, thereby causing a current to flow between the wires, and measuring the electrical resistance therebetween.

The wires 10 are capable of conducting electricity, compatible with the fuel cell environment, and can be conventional. Since the electrochemical sensor 40 operates similar to a hydrogen reference electrode where hydrogen is evolved on the surface of one of the wires through a water electrolysis reaction occurring thereon, these wires 10 should be catalytically active, either inherently or the surface of the wires can be catalyzed by conventional means such as platinization, coating, or the use of a catalyzed rolled screen positioned around and in contact with the wires 10. Some possible wires 10 include: noble metal based wires and noble metal alloy wires such as gold based, iridium based, palladium based, platinum based, ruthenium based, rubidium based, rhodium based, alloys thereof, and others. The size of these wires 10, which is readily determined by an artisan, is dependent upon the specific application since the wires must be sufficiently small to fit into the desired location without physically contacting each other. For example, in a phosphoric acid fuel cell, the electrochemical sensor 40 typically occupies an about 1.6 millimeters (mm) wide groove in the electrolyte reservoir plate. As a result, about 0.2 mm to about 0.5 mm constitutes the preferred wire diameter, with about 0.35 mm to about 0.40 mm especially preferred.

In order to monitor the electrolyte resistance between the wires 10, an electrical circuit must be formed and maintained between the wires 10. Consequently, the wires 10 can be oriented in any manner, with respect to one another, which allows current flow between them. Clearly, maintenance of this circuit requires sufficient distance between the wires 10 to avoid direct physical contact therebetween which will cause short circuiting. In other words, it is necessary to maintain sufficient resistance between the wires, typically above about 1 ohm. For convenience of constructing the electrochemical sensor 40, its installation and use, the wires 10 are preferably positioned substantially parallel to one another as is shown in FIGS. 2 and 3.

The circuit between the wires 10 is completed using a porous, electrically non-conductive conduit 50 which functions as a vehicle for electrolyte to move from the electrolyte reservoir plate 70 to the wires 10 through capillary forces. Since the electrical resistance between the wires 10 relates to the electrolyte content in the conduit 50, it is important for the volume percent of electrolyte in the conduit 50 to be similar to that in the electrolyte reservoir plate 70 such that a determination of electrolyte content in the conduit 50 will be representative of the electrolyte content in the electrolyte reservoir plate 70. Therefore, a similar pore size distribution in the conduit 50 as in the electrolyte reservoir plate 70 is preferred to ensure the capillary forces in each will be similar, thereby enabling a similar rate of electrolyte migration from each. If the conduit 50 has a significantly smaller pore size distribution than the electrolyte reservoir plate 70, the conduit 50 will retain a greater electrolyte content than the electrolyte reservoir plate 70, thereby resulting in a large error margin and possibly an electrolyte content reading wholly unrelated to the actual electrolyte content in the electrolyte reservoir plate 70. Similarly, if the pore size distribution in the conduit 50 is significantly greater than that in the electrolyte reservoir plate 70, the electrolyte will first migrate from the conduit 50, thereby again resulting in a large error margin or a wholly incorrect electrolyte content reading.

Additionally, since the electrical resistance is determined between the wires 10, it is important that the electrolyte content between the wires 10 be similar to that in the electrolyte reservoir plate 70. Consequently, the wires 10 should physically contact the conduit 50 such that the pore size distribution at the interface between the wires 10 and the conduit 50 is similar to the pore size distribution of the electrolyte reservoir plate 70, thereby ensuring that a similar electrolyte content is maintained between the wires 10 as in the electrolyte reservoir plate 70. As explained above, capillary forces will cause electrolyte to be wicked away from the wires 10 at a greater rate than the electrolyte migration from the electrolyte reservoir plate 70 if the pore size distribution at the wires 10 is greater than that in the electrolyte reservoir plate 70 while electrolyte will be wicked away from the wire 10 slower than the electrolyte migrates from the electrolyte reservoir plate 70 if the pore size distribution is smaller between the wires 10 than in the electrolyte reservoir plate 70.

Possible conduits 50 comprise porous means which are compatible with the operating environment, including: carbides, such as silicon carbide, titanates, such as potassium titanate, aluminates, and mixtures thereof, among other porous means commonly known in the art. For example, LONZA® F-360, a silicon carbide produced by Lonza Inc., Fairlawn, Jersey, has proven particularly useful with phosphoric acid fuel cells since it has a mean particle size of about 20 microns to about 25 microns. LONZA F-350, therefore, forms a mean pore diameter of about 5 microns to about 15 microns which is similar to the electrolyte reservoir plate mean pore size of about 10 microns to about 20 microns.

In addition to functioning as a vehicle for electrolyte flow between the wires 10 and the electrolyte containing body 70, the conduit 50 can also function as a support for the wires 10. In both functions, the desired physical contact between the wires 10, the conduit 50, and the electrolyte containing body 70, is preferably obtained using the conduit 50 in the form of a pliable paste. The pliable paste can be formed by adding a liquid compatible with the electrochemical sensor 40 and the fuel cell environment to the conduit 50. For example, phosphoric acid can be added to the silicon carbide (LONZA F-360) for use in a phosphoric acid fuel cell. The pliable paste is then molded to conform to the shape of the electrolyte containing body 70 such that assembly of the electrochemical sensor comprises placing the conduit 50 in the electrolyte containing body groove 60, positioning the wires 10 on the conduit 50 so as not to physically contact each other, and placing additional conduit 50 over the wires.

Using the conduit 50 in the form of a pliable paste, however, prevents calibration of the electrochemical sensor 40 prior to insertion into the fuel cell since the wires are placed in a portion of the pliable paste positioned within the groove 60 or the pliable paste is applied to the opening 30 once the sheath 20 is in the electrolyte containing body 70. If it is desired to calibrate the electrochemical sensor 40 prior to insertion into a fuel cell, a rigid conduit rather than a paste can be employed. The geometry of such an electrochemical sensor would be expected to be unchanged between the time of fabrication and its use in a fuel cell, thereby rendering a calibration before insertion suitable for later use. However, such an electrochemical sensor is more difficult to fabricate and may result in loss of physical contact between the electrochemical sensor wires, the conduit, and the electrolyte containing body, with time. Consequently, the use of a rigid conduit is less desirable, but is contemplated by this invention.

When the pliable conduit is employed, it is preferred to utilize a separate, chemically inert, electrically non-conductive sheath 20 to substantially encapsulate and support the wires 10 since the wire placement in the pliable paste is difficult and impractical. This sheath 20 forms an encasement around the wires 10 to prevent physical contact between the wires themselves and to prevent physical contact between the wires 10 and the electrolyte containing body 70. In this embodiment of the invention, the conduit 50 is located in the opening 30 in the sheath 20 so as to physically contact the wires 10.

Possible sheaths 20 include polymer based, such as fluoro-polymer based, ceramic based, polyetheretherketone, mixtures thereof, and other conventional support means. Some fluoro-polymer sheaths include TEFLON® (polytetrafluoro ethylene) produced by E. I. du Pont de Nemours, E. I. & Company, Wilmington, Del., FLUOREL® produced by 3M Corporation, St. Paul, Minn., fluorinated ethylene propylene, and others. A common ceramic based sheath is alumina. The preferred sheath 20 depends upon the application and operating conditions under which the sheath 20 is to be used. For example, in a molten carbonate fuel cell, a ceramic sheath is preferred due to its high temperatures tolerance, while in a phosphoric acid fuel cell, a TEFLON sheath is preferred due to its chemical stability and flexibility.

The dimensions and geometry of the sheath 20 are also application dependent with factors such as wire size and the size of the electrolyte containing body groove 60 being important. The sheath 20 is preferably sufficiently large to encapsulate, support, and hold the wires 10 stably in the electrolyte containing body groove 60. For example, for a phosphoric acid fuel cell, the sheath 20 can be straight and flexible, having dimensions of about 20 centimeters (cm) to about 40 cm in length, and about 1.5 mm to about 2.5 mm in width, with substantially parallel holes running the length of the sheath 20 where the wires 10 are located. The electrochemical sensor 40 can be placed in a frame which surrounds the fuel cell component provided the electrochemical sensor 40 has access to the cell's electrolyte. Another example comprises placing the electrochemical sensor 40 in a frame which surrounds the fuel cell component such that the electrochemical sensor 40 has access to electrolyte. Under such conditions, the electrochemical sensor 40's dimensions and geometry may be significantly different, possibly requiring a thinner, shorter sheath 20 and smaller wires 10.

Use of the sheath 20 comprises locating the conduit 50 in an opening 30 of the sheath 20 such that the conduit 50 physically contacts the wires 10, and when in use, also physically contacts the electrolyte reservoir plate 70 such that the electrolyte in the electrolyte reservoir plate 70 will be wicked into the conduit 50 thereby forming an electrical connection between the wires 10. The opening 30 of the sheath 20 is preferably sufficiently large such that the amount of the wires 10 exposed to the conduit 50 does not limit the rate of the electrochemical reaction which occurs thereon since the rate of reaction is directly proportional to the amount of wire in physical contact with the conduit 50. As the amount of contacted wire decreases, the rate of reaction decreases, and the error margin in determining the electrolyte content increases. Typically, the opening 30 is located close to the end of the sheath 20 which is inserted into the electrolyte containing body 70, about 0.6 cm to about 5 cm from the end of the sheath 20, with about 1.2 cm to about 4 cm preferred.

The wires 10 which typically protrude from the end of the electrochemical sensor 40 at the end of the sheath 20 furthest from the opening 30, are routed through the anode and cathode chambers of the fuel cell and connected to the volt meter and the electrical current supply (shown as 80, FIG. 2) which function as a means for measuring electrical resistance between the wires 10. These can be any conventional means for measuring electrical resistance such as current interruption and AC impedance spectroscopy. The AC impedance spectroscopy can be performed with a Solartron 1250 Frequency Response Analyzer with a Solartron 1286 Electrochemical Interface, produced by Solartron Instruments, Farnborough Hampshire, England, a division of Schlumberger Electronics (UK) Ltd.

Due to variations in the geometry of the electrochemical sensor opening 30 and the conduit 50, it is preferred to calibrate the electrochemical sensor 40 in situ. Therefore, the fuel cell stack is run for a sufficient period of time to reach steady state, typically about 100 hours. Once at steady state, the fuel cell stack is shutdown and an electrochemical sensor reading is taken using AC impedance spectroscopy by applying an alternating voltage signal to the wires to produce an alternating current and varying the frequency of the alternating current until the phase shift between the current and the voltage goes to zero. The fuel cell is again started and a second reading is taken. These two readings are used to determine the electrolyte content of the electrolyte reservoir plate 70 based upon the relationship between the electrolyte content and the electrical resistance between the wires 10.

Since Ohm's law states that the voltage (v) is directly proportional to the electrical resistance (R) times the current (i), at a phase shift of zero the impedance and the electrical resistance between the wires 10 are equivalent. Consequently, the electrical resistance is equivalent to the ratio of the voltage to the current.

$$v = R * i$$

This electrical resistance has been found to be inversely proportional to the 2.2 power of the percentage of the reservoir plate pore volume filled with electrolyte (V). The quantity ($R_o$) is the reference resistance and ($C_o$) is the reference conductivity when the pore volume is filled to the percentage ($V_o$). The electrolyte conductivity (C) is included since the resistance must be corrected for changes in electrolyte conductivity between the reference state at which the measurements are being taken due to changes in temperature and dew point.

$$\frac{R}{R_o} = \frac{C_o}{C} \left( \frac{V_o}{V} \right)^{2.2}$$

As a result, as the amount of electrolyte increases or decreases in the electrolyte reservoir plate 70, the electrolyte content in the conduit 50 similarly changes. This change in electrolyte content can be monitored by monitoring the change in the electrical resistance across the wires 10. If a polymeric electrolyte such as NAFION® is used in the probe, the resistance is a measure of the dew point of the anode electrode or cathode electrode reactant gases (oxidant and fuel gases) at a given temperature, in the opening FIG. 4 shows experimental data obtained using the electrochemical sensor 40 at various fuel cell current densities. Electrochemical sensor readings obtained at the cathode are shown as positive currents and those at the anode as negative currents for graphical purposes. The percentage of pore volume in the electrolyte reservoir plate 70 filled with electrolyte can be seen to increase on the anode side and decrease on the cathode side as the current density is increased, thereby revealing the migration of the electrolyte from the cathode electrode to the anode electrode.

Prior to the electrochemical sensor of the present invention, the degree of the electrolyte migration problem within a fuel cell had not been quantified. With the electrochemical sensor of the present invention, electrolyte migration within the fuel cell can be monitored during fuel cell operation. Information obtained with the electrochemical sensor can lead to a better understanding of fuel cells, inefficiencies therewith, and also to possible solutions and improvements. Shedding light on the electrolyte migration problem is a major step toward a solution.

The data from the electrolyte sensor can further be useful in preventing fuel cell damage. For instance, some fuel cells require the addition of electrolyte during operation to prevent cross-over or mixing of the fuel and oxidant gases. Electrolyte content information obtained with the electrochemical sensor can be employed to determine if and when additional electrolyte should be added to the fuel cell. Furthermore, resistivity in the fuel cell during shutdown establishes possible electrolyte freezing which can severely damage the anode and cathode electrodes. As the electrolyte cools and begins to freeze the electrical resistance between the wires increases, thereby signaling potential electrode damage.

Although this invention has been shown and described with respect to detailed embodiments thereof, it will be understood by those in the art that various changes in form and detail thereof may be made without departing from the spirit and scope of the claimed invention.

I claim:

1. An electrochemical sensor for monitoring the electrolyte content in an electrolyte containing body, comprising:
   a. at least two electrically conductive wires, wherein sufficient space exists between said wires so as to prevent short circuiting of said wires;
   b. a porous, electrically non-conductive conduit in physical contact with said wires and having a similar pore size distribution as the electrolyte containing body; and
   c. a means for measuring electrical resistance between said wires.

2. An electrochemical sensor as in claim 1 wherein said wires are noble metal based wires or noble metal alloy wires.

3. An electrochemical sensor as in claim 2 wherein said wire is gold based, iridium based, palladium based, platinum based, ruthenium based, rubidium based, rhodium based, or an alloy thereof.

4. An electrochemical sensor as in claim 1 further comprising a sheath substantially encapsulating said wires, wherein said conduit is located in an opening in said sheath.

5. An electrochemical sensor as in claim 4 wherein said sheath is polymer based, ceramic based, or a mixture thereof.

6. An electrochemical sensor as in claim 5 wherein said sheath is TEFLON, FLUOREL, alumina, or a mixture thereof.

7. An electrochemical sensor as in claim 1 wherein said conduit is a carbide, titanate, aluminate, or a mixture thereof.

8. An electrochemical sensor as in claim 1 wherein said means for measuring electrical resistance between said wires is a current interruption means or a means for performing alternating current impedance spectroscopy.

9. An improved fuel cell system having an anode electrode, a cathode electrode, an electrolyte disposed therebetween, an anode chamber, a cathode chamber, and at least one electrolyte reservoir plate, wherein the improvement comprises: an electrochemical sensor for monitoring electrolyte content in the electrolyte reservoir plate, said electrochemical sensor having,
   a. at least two electrically conductive wires, wherein sufficient space exists between said wires so as to prevent short circuiting of said wires;
   b. a porous, electrically non-conductive conduit having a similar pore size distribution as the electrolyte reservoir plate, wherein said conduit physically contacts said wires and said electrolyte reservoir plate; and
   c. a means for measuring electrical resistance between said wires;
whereby electrolyte in said electrolyte reservoir plate is wicked into said porous means such that upon application of a voltage across said wires, a current passes between said wires through said electrolyte in said porous means.

10. An improved fuel cell system as in claim 9 wherein said means for measuring electrical resistance between said wires is a current interruption means or a means for performing alternating current impedance spectroscopy.

11. An improved fuel cell system as in claim 9 wherein said wires are noble metal based wires or noble metal alloy wires.

12. An improved fuel cell system as in claim 11 wherein said wire is gold based, iridium based, palladium based, platinum based, ruthenium based, rubidium based, rhodium based, or an alloy thereof.

13. An improved fuel cell system as in claim 9 further comprising a sheath substantially encapsulating said wires, wherein said conduit is located in an opening in said sheath.

14. An improved fuel cell system as in claim 13 wherein said sheath is polymer based, ceramic based, or a mixture thereof.

15. An improved fuel cell system as in claim 14 wherein said sheath is TEFLON, FLUOREL, alumina, or a mixture thereof.

16. An improved fuel cell system as in claim 9 wherein said conduit is a carbide, titanate, aluminate, or a mixture thereof.

17. A method for monitoring electrolyte content, comprising the steps of:
   a. using an electrochemical sensor having at least two electrically conductive wires and a porous, electrically non-conductive conduit, wherein sufficient space exists between said wires so as to prevent short circuiting of said wires, and said wires are connected to a means measuring electrical resistance between said wires;
   b. physically contacting said conduit and an electrolyte containing body;
   c. drawing electrolyte into said conduit from said electrolyte containing body via capillary forces;
   d. applying a voltage across said wires with said means for measuring electrical resistance; and
   e. measuring the electrical resistance between said wires;
whereby the electrical resistance between said wires is related to the electrolyte content within the electrolyte containing body.

18. A method for monitoring electrolyte content as in claim 17 wherein said wires are noble metal based wires or noble metal alloy wires.

19. A method for monitoring electrolyte content as in claim 18 wherein said wire is gold based, iridium based, palladium based, platinum based, ruthenium based, rubidium based, or an alloy thereof.

20. A method for monitoring electrolyte content as in claim 17 wherein said electrochemical sensor further comprises a sheath substantially encapsulating said wires, wherein said conduit is located in an opening in said sheath.

21. A method for monitoring electrolyte content as in claim 20 wherein said sheath is polymer based, ceramic based, or a mixture thereof.

22. A method for monitoring electrolyte content as in claim 21 wherein said sheath is TEFLON, FLUOREL, alumina, or a mixture thereof.

23. A method for monitoring electrolyte content as in claim 17 wherein said conduit is a carbide, titanate, aluminate, or a mixture thereof.

24. A method for monitoring electrolyte content as in claim 17 wherein said voltage causes an alternating current to flow through said wires.

\* \* \* \* \*